(12) United States Patent
Shigihara et al.

(10) Patent No.: US 10,136,858 B2
(45) Date of Patent: Nov. 27, 2018

(54) METHOD FOR INSPECTING PRESSURE PULSE WAVE SENSOR AND METHOD FOR MANUFACTURING PRESSURE PULSE WAVE SENSOR

(71) Applicant: OMRON HEALTHCARE Co., Ltd., Kyoto (JP)

(72) Inventors: Noriko Shigihara, Kyoto (JP); Yuki Kato, Kyoto (JP); Masayuki Wakamiya, Kyoto (JP); Toshihiko Ogura, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 15/914,711

(22) Filed: Mar. 7, 2018

(65) Prior Publication Data
US 2018/0192956 A1 Jul. 12, 2018

Related U.S. Application Data

(63) Continuation of application No. PCT/JP2016/075435, filed on Aug. 31, 2016.

(30) Foreign Application Priority Data

Sep. 7, 2015 (JP) .................................. 2015-175967

(51) Int. Cl.
*A61B 5/00* (2006.01)
*G01L 27/00* (2006.01)
(Continued)

(52) U.S. Cl.
CPC .............. *A61B 5/6843* (2013.01); *A61B 5/02* (2013.01); *A61B 5/022* (2013.01); *A61B 5/0245* (2013.01); *G01L 27/002* (2013.01)

(58) Field of Classification Search
CPC ..... G01L 27/002; A61B 5/6843; A61B 5/022; A61B 5/0245; A61B 5/02
See application file for complete search history.

(56) References Cited

U.S. PATENT DOCUMENTS

| 4,809,536 A | 3/1989 | Nishiguchi |
| 5,179,956 A | 1/1993 | Harada et al. |
| (Continued) | | |

FOREIGN PATENT DOCUMENTS

| JP | S63-118629 A | 5/1988 |
| JP | H02-025050 A | 1/1990 |
| (Continued) | | |

OTHER PUBLICATIONS

International Search Report issued in Application No. PCT/JP2016/075435, dated Nov. 8, 2016 (6 pages).
(Continued)

*Primary Examiner* — Seahvosh Nikmanesh
(74) *Attorney, Agent, or Firm* — Osha Liang LLP

(57) ABSTRACT

A method for inspecting a pressure pulse wave sensor is provided. The sensor chip includes a recess which is recessed in a direction perpendicular to the pressure-sensitive face, and the pressure-sensitive element array is formed in a portion of the sensor chip whose thickness is reduced in the direction due to the recess. The method includes: bonding and fixing the sensor chip onto the substrate so that the recess communicates with atmospheric air through only the through hole of the substrate; connecting a substrate-side terminal portion of the substrate and the chip-side terminal portion through an electrically conductive member; and performing characteristic evaluation on the sensor chip based on a signal outputted from the substrate-side terminal
(Continued)

portion in a state in which air is sucked through the through hole of the substrate to thereby apply negative pressure to the pressure-sensitive face.

4 Claims, 5 Drawing Sheets

(51) Int. Cl.
*A61B 5/022* (2006.01)
*A61B 5/0245* (2006.01)
*A61B 5/02* (2006.01)

(56) References Cited

U.S. PATENT DOCUMENTS

| | | | | |
|---|---|---|---|---|
| 6,159,166 A | * | 12/2000 | Chesney | A61B 5/021 381/173 |
| 2006/0047207 A1 | | 3/2006 | Itonaga et al. | |
| 2007/0118038 A1 | | 5/2007 | Bodecker et al. | |
| 2007/0118039 A1 | | 5/2007 | Bodecker et al. | |
| 2010/0174201 A1 | | 7/2010 | Bodecker et al. | |
| 2010/0185103 A1 | | 7/2010 | Bodecker et al. | |
| 2011/0201948 A1 | | 8/2011 | Bodecker et al. | |
| 2011/0201949 A1 | | 8/2011 | Bodecker et al. | |
| 2014/0058276 A1 | | 2/2014 | Bodecker et al. | |
| 2014/0081158 A1 | | 3/2014 | Bodecker et al. | |
| 2016/0310021 A1 | | 10/2016 | Kato et al. | |

FOREIGN PATENT DOCUMENTS

| | | |
|---|---|---|
| JP | H04-067839 A | 3/1992 |
| JP | 2004-188183 A | 7/2004 |
| JP | 2009-517137 A | 4/2009 |
| JP | 2015-144628 A | 8/2015 |

OTHER PUBLICATIONS

Written Opinion issued in Application No. PCT/JP2016/075435, dated Nov. 8, 2016 (4 pages).

International Preliminary Report on Patentability issued in Application No. PCT/JP2016/075435, dated Jul. 14, 2017 (7 pages).

* cited by examiner

METHOD FOR INSPECTING PRESSURE PULSE WAVE SENSOR AND METHOD FOR MANUFACTURING PRESSURE PULSE WAVE SENSOR

CROSS-REFERENCE TO RELATED APPLICATION(S)

This application is a continuation of PCT application No. PCT/JP2016/075435, which was filed on Aug. 31, 2016 based on Japanese Patent Application (No. 2015-175967) filed on Sep. 7, 2015, the contents of which are incorporated herein by reference.

BACKGROUND

1. Technical Field

The present invention relates to a method for inspecting a pressure pulse wave sensor and a method for manufacturing a pressure pulse wave sensor.

2. Background Art

Generally, a press type pressure measurement device is known to press against an object to be measured to thereby measure contact pressure against the object to be measured. A pulse wave measurement device is provided as a device to which the press type pressure measurement device is applied.

The pulse wave measurement device is a device in which a substrate having pressure-sensitive elements is pressed against a body surface to thereby measure a pressure pulse wave occurring in an artery located at a comparatively shallow position from skin in vivo. In order to know a health condition of a person to be examined, it is very important to measure a pressure pulse wave of the person to be examined using such a pulse wave measurement device.

A pressure sensor chip using a strain gauge or a diaphragm as the pressure-sensitive element is generally used in the press type pulse wave measurement device. For example, JP-A-2004-188183 discloses this kind of press type pulse wave measurement device.

A pulse wave detection device mounted with a pressure sensor chip has been described in JP-A-2004-188183. In the pulse wave detection device, a diaphragm is formed on a flat plate-like semiconductor substrate, and electric terminals on a front face of the semiconductor substrate and electric terminals on a flexible board are connected to each other respectively through a brazing material.

The diaphragm has a configuration in which a plurality of pressure-sensitive elements are arranged in one direction. In the configuration, wires extend respectively from the pressure-sensitive elements toward opposite sides in a perpendicular direction perpendicular to the one direction, and the flexible board is connected to end portions of the wires.

In addition, methods for performing characteristic inspection on the pressure sensor chip have been described in JP-A-02-025050 and JP-A-63-118629. In each of the methods, a pressure chamber of the pressure sensor chip with a diaphragm structure, which is in a wafer state, is sucked from its back face so that negative pressure is applied to the diaphragm to thereby perform the characteristic inspection on the pressure sensor chip.

The pressure sensor chip used in the pulse wave measurement device is pressed against skin in a state in which a pressure-sensitive element array including the plurality of pressure-sensitive elements arranged in the one direction intersects with a traveling direction of an artery. In the pulse wave measurement device, after the pressure sensor chip is positioned on the artery in order to determine an optimum pressure-sensitive element and optimum pressing force, a pressure pulse wave is detected based on a pulse wave signal outputted from the optimum pressure-sensitive element in the optimum pressing force.

For this reason, in order to determine the optimum pressure-sensitive element, the plurality of pressure-sensitive elements in the pressure sensor chip used in the pulse wave measurement device are requested to be uniform in detection sensitivity with one another so that any of the pressure-sensitive elements can detect a pressure pulse wave in the same conditions.

By an adhesive material of a resin etc., the pressure sensor chip including the pressure-sensitive element array is fixed to the substrate on which wiring terminals are provided to be electrically connected to electric terminals of the pressure sensor chip.

When the adhesive material for bonding the pressure sensor chip and the substrate to each other is deformed due to temperature and humidity in this case, stress may be applied to the pressure sensor chip due to a change in environment. When such stress occurs, a variation in detection sensitivity is generated among the respective pressure-sensitive elements in the pressure-sensitive element array, thereby making it difficult to detect the pressure pulse wave accurately.

Therefore, in the pressure sensor chip used in the pulse wave measurement apparatus, characteristic inspection in the state in which the pressure sensor chip is fixed to the substrate is important.

JP-A-2004-188183 gives no description about such characteristic inspection of the pressure sensor chip.

Each of the inspection methods described in JP-A-02-025050 and JP-A-63-118629 serves for inspecting the pressure sensor chip in the wafer state. For this reason, it is impossible to know a characteristic in a state in which a strain is applied to the diaphragm due to the aforementioned adhesive material.

In addition, neither of JP-A-02-025050 and JP-A-63-118629 is about a pressure sensor chip assumed to measure a pulse wave, and recognizes importance of inspection performed in a state in which the pressure sensor chip is fixed to a substrate.

SUMMARY

The invention has been accomplished in consideration of the aforementioned circumstances. An object of the invention is to provide an inspection method and a manufacturing method of a pressure pulse wave sensor, in which it is possible to know an influence of a change in usage environment on detection accuracy of a pressure pulse wave.

According to an aspect of the invention, there is provided a method for inspecting a pressure pulse wave sensor which includes a sensor chip and a substrate, the sensor chip including a pressure-sensitive element array constituted by a plurality of pressure-sensitive elements arranged in one direction, the sensor chip put into use so that a pressure-sensitive face of the sensor chip where the pressure-sensitive element array is formed is pressed against a body surface of a living body in a state in which the one direction intersects with a traveling direction of an artery of the living body, the sensor chip fixed to the substrate, wherein the substrate includes a through hole and a substrate-side terminal portion, the sensor chip includes a recess which is recessed in a direction perpendicular to the pressure-sensitive face and on an opposite side to the pressure-sensitive face, and the pressure-sensitive element array is formed on the pressure-sensitive face in a portion of the sensor chip whose thickness is reduced in the perpendicular direction due to the recess, and the sensor chip further includes a chip-side terminal portion which is electrically connected to the pressure-sensitive element array and which is provided at one or each of opposite ends of the pressure-sensitive element array extending in the one direction, the method comprising: bonding and fixing the sensor chip onto the substrate so that the recess communicates with atmospheric air through only the through hole of the substrate; connecting the substrate-side terminal portion of the substrate to which the sensor chip is bonded and fixed, and the chip-side terminal portion through an electrically conductive member; covering the electrically conductive member with a protective member; and performing characteristic evaluation about a variation among the plurality of pressure-sensitive elements of the sensor chip, after covering the electrically conductive member with the protective member, based on a signal outputted from the substrate-side terminal portion in a state in which air is sucked through the through hole of the substrate to thereby apply negative pressure to the pressure-sensitive face.

According to an aspect of the invention, there is also provided a method for manufacturing a pressure pulse wave sensor which includes a sensor chip and a substrate, the sensor chip including a pressure-sensitive element array constituted by a plurality of pressure-sensitive elements arranged in one direction, the sensor chip put into use so that a pressure-sensitive face of the sensor chip where the pressure-sensitive element array is formed is pressed against a body surface of a living body in a state in which the one direction intersects with a traveling direction of an artery of the living body, the sensor chip fixed to the substrate, wherein a through hole and a substrate-side terminal portion are formed in the substrate, a recess which is recessed in a direction perpendicular to the pressure-sensitive face and on an opposite side to the pressure-sensitive face is formed in the sensor chip, and the pressure-sensitive element array is formed on the pressure-sensitive face in a portion of the sensor chip whose thickness is reduced in the perpendicular direction due to the recess, and a chip-side terminal portion which is electrically connected to the pressure-sensitive element array is further formed at one or each of opposite ends of the pressure-sensitive element array extending in the one direction in the sensor chip, the method comprising: bonding and fixing the sensor chip onto the substrate so that the recess communicates with atmospheric air through only the through hole of the substrate; connecting the substrate-side terminal portion of the substrate to which the sensor chip is bonded and fixed, and the chip-side terminal portion through an electrically conductive member; covering the electrically conductive member with a protective member; performing characteristic evaluation about a variation among the plurality of pressure-sensitive elements of the sensor chip, after covering the electrically conductive member with the protective member, based on a signal outputted from the substrate-side terminal portion in a state in which air is sucked through the through hole of the substrate to thereby apply negative pressure to the pressure-sensitive face; and forming a protective layer protecting both the sensor chip which is determined as accepted based on a result of the characteristic evaluation, and the protective member which covers the electrically conductive member which connects the chip-side terminal portion of the sensor chip and the substrate-side terminal portion.

DESCRIPTION OF EXEMPLARY EMBODIMENTS

An embodiment of the invention will be described below with reference to the drawings.

Figure 1:
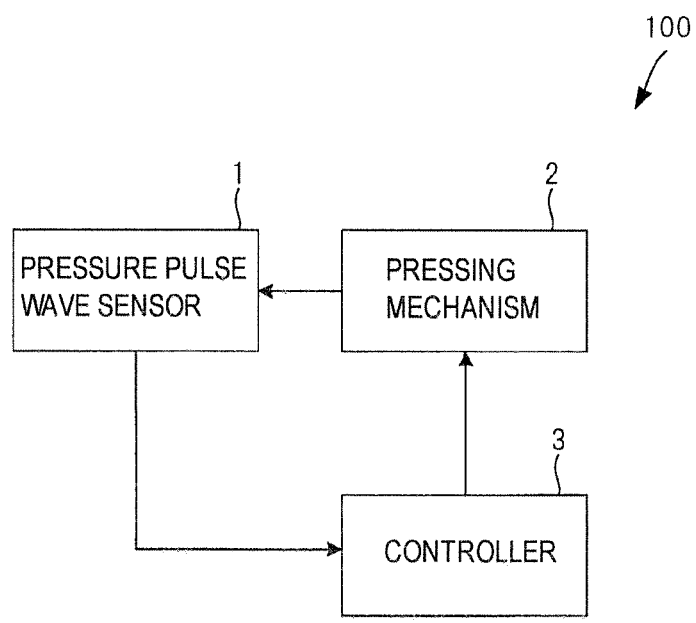
FIG. 1 is a block diagram showing the configuration of a blood pressure measurement device 100 as a biological information measurement device in order to explain an embodiment of the invention.

FIG. 1 is a block diagram showing the configuration of a blood pressure measurement device 100 as a biological information measurement device in order to explain the embodiment of the invention. The blood pressure measurement device 100 is, for example, a wrist-worn type which is used to be worn on a wrist.

The blood pressure measurement device 100 includes pressure pulse wave sensors 1, a pressing mechanism 2 and a controller 3. The pressing mechanism 2 serves for pressing the pressure pulse wave sensors 1 against a body surface of a person to be examined. The controller 3 controls the pressing mechanism based on a signal outputted from each of the pressure pulse wave sensors 1, or calculates biological information including blood pressure of the person to be examined based on the signal.

Figure 2:
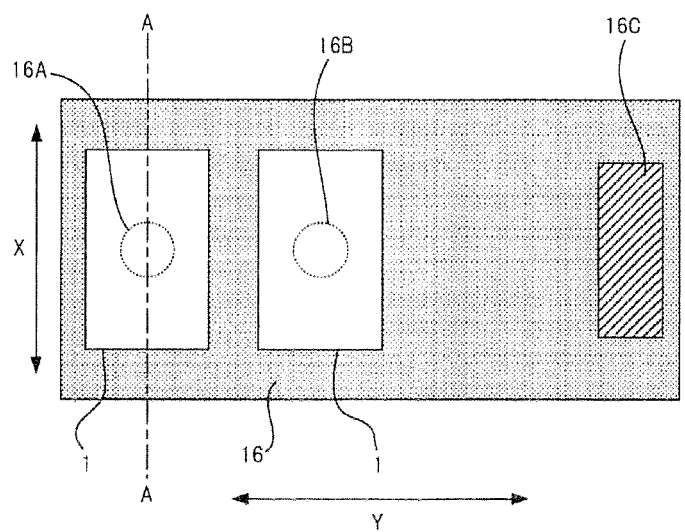
FIG. 2 is a plan view of a flexible board 16 on which pressure pulse wave sensors 1 shown in FIG. 1 are mounted.

FIG. 2 is a plan view of a flexible board 16 on which the pressure pulse wave sensors 1 shown in FIG. 1 are mounted.

The flexible board 16 is shaped like a rectangle whose longitudinal direction corresponds to a direction Y. The direction Y is perpendicular to a direction X serving as one direction. The two pressure pulse wave sensors 1 and a connector 16C are mounted on a front face of the flexible board 16.

Wires which are connected to connection terminals of the two pressure pulse wave sensors 1 respectively are provided inside a resin film of the flexible board 16. The respective wires are led to the connector 16C. The connector 16C, and a connector of a not-shown circuit board in which the controller 3 etc. in FIG. 1 is formed are connected to each other.

In addition, the flexible board 16 has through holes 16A and 16B provided substantially at the centers of regions in which the two pressure pulse wave sensors 1 are mounted respectively. The through holes 16A and 16B will be described later.

Figure 3:
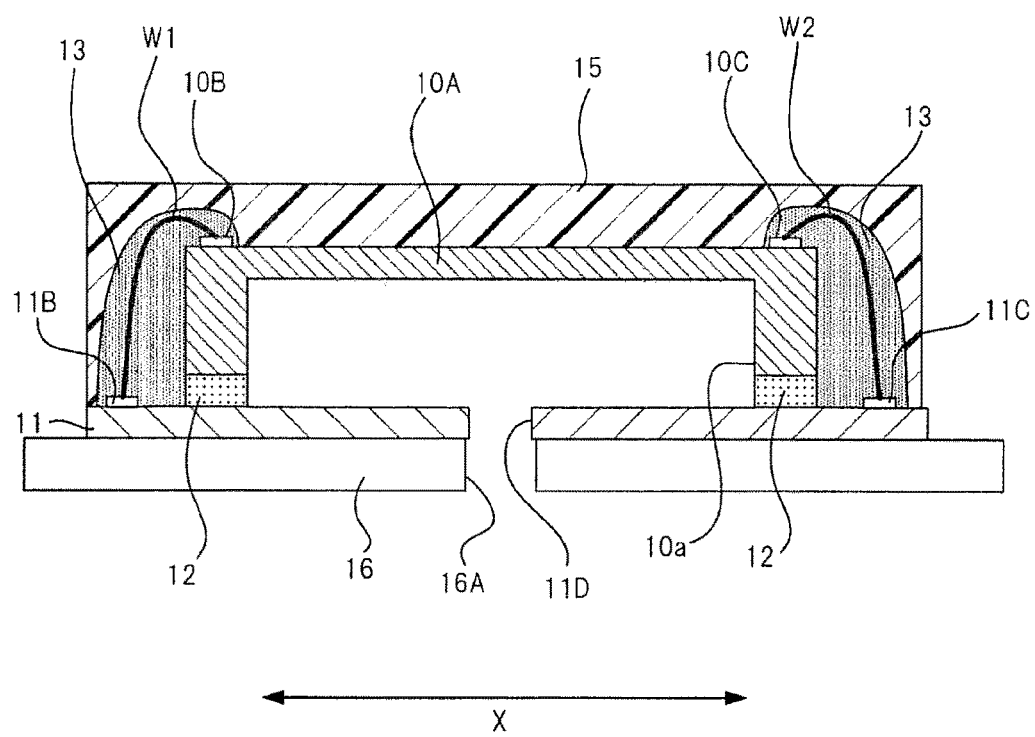
FIG. 3 is a schematic view of a section taken along a line A-A shown in FIG. 2.
Figure 4:
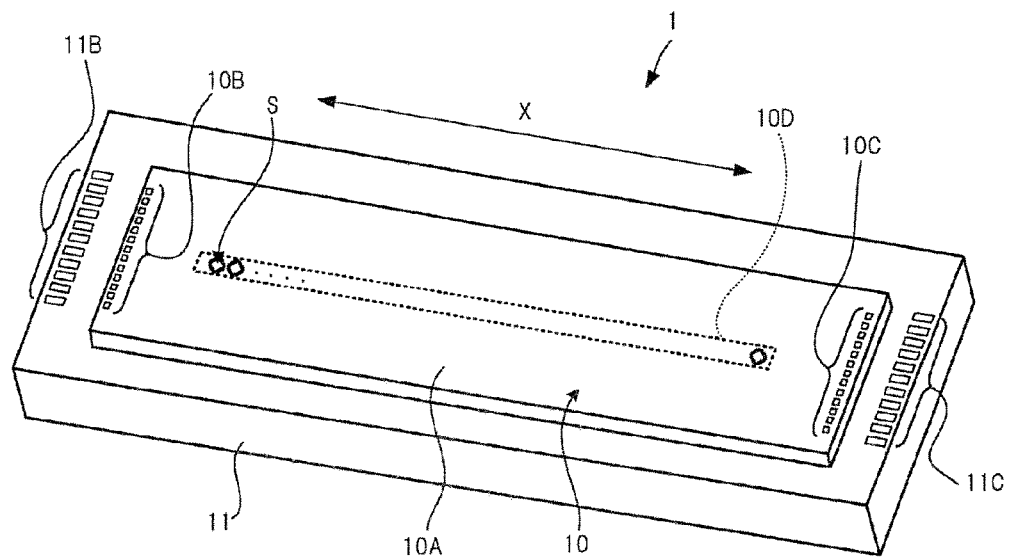
FIG. 4 is a perspective view showing a main part configuration of the pressure pulse wave sensor 1 which is seen from a side contacting with skin.

FIG. 3 is a schematic view of a section taken along a line A-A shown in FIG. 2. FIG. 4 is a perspective view showing a main part configuration of the pressure pulse wave sensor 1 which is seen from a side contacting with skin. In FIG. 4, illustration of some of constituent elements is omitted. In FIG. 3, constituent elements except the flexible board 16 constitute the pressure pulse wave sensor 1.

As shown in FIG. 4, the pressure pulse wave sensor 1 includes a sensor chip 10 and a flat plate-like substrate 11.

The sensor chip 10 includes a semiconductor substrate 10A made of a silicon single crystal, a single crystal of a compound semiconductor such as gallium arsenide, etc. The semiconductor substrate 10A is shaped like a rectangle whose longitudinal direction corresponds to the direction X.

The substrate 11 is constituted by a rigid substrate sufficiently higher in rigidity than the semiconductor substrate 10A made of a ceramic substrate, a glass substrate etc. The substrate 11 is shaped like a rectangle whose longitudinal direction corresponds to the direction X.

As shown in FIG. 4, a plurality of pressure-sensitive elements S for detecting contact pressure are arranged in the direction X on a front face (a face contacting with skin of a living body) of the semiconductor substrate 10A. Each of the pressure-sensitive elements S includes a bridge having four strain-resistance elements. A pressure-sensitive element array 10D is constituted by the plurality of pressure-sensitive elements S which are arranged side by side in the direction X. Incidentally, illustration of the pressure-sensitive elements S is omitted in FIG. 3.

As shown in FIG. 3, in the semiconductor substrate 10A, a recess 10a is formed in an opposite face to the face (hereinafter referred to as pressure-sensitive face) where the pressure-sensitive element array 10D is formed. The recess 10a is recessed in a direction (hereinafter referred to as sensor pressing direction) perpendicular to the pressure-sensitive face.

The semiconductor substrate 10A is configured to have a thin portion (diaphragm) whose thickness in the sensor pressing direction is thinner than any other portion due to the recess 10a. The pressure-sensitive element array 10D is formed in a region of the pressure-sensitive face opposite to the bottom of the recess 10a.

Of the opposite face (in other words, the face where the recess 10a is formed) of the semiconductor substrate 10A to the pressure-sensitive face, the other portion than the recess 10a is fixed to a front face of the substrate 11 by an adhesive material 12. For example, a resin-based material made of an ultraviolet curing resin can be used as the adhesive material 12.

The semiconductor substrate 10A is fixed to the front face of the substrate 11 so that the recess 10a of the semiconductor substrate 10A can communicate with atmospheric air through only a through hole 11D formed in the substrate 11.

Of the two pressure pulse wave sensors 1 of the blood pressure measurement device 100, one pressure pulse wave sensor 1 is mounted on the flexible board 16 so that the through hole 11D and the through hole 16A overlap each other in a plan view seen from the pressure-sensitive face side. In addition, of the two pressure pulse wave sensors 1 of the blood pressure measurement device 100, the other pressure pulse wave sensor 1 is mounted on the flexible board 16 so that a through hole 11D and the through hole 16B overlap each other in the same plan view.

With this configuration, a space partitioned by the semiconductor substrate 10A, the adhesive material 12 and the substrate 11 in the pressure pulse wave sensor 1 is maintained at atmospheric pressure (reference pressure) due to the through hole 11D of the substrate 11 and the through hole 16A (or the through hole 16B) of the flexible board 16.

A first terminal portion 10B and a second terminal portion 10C electrically connected to the pressure-sensitive element array 10D are disposed on opposite end portions of the pressure-sensitive face of the semiconductor substrate 10A in the direction X. Each of the first terminal portion 10B and the second terminal portion 10C is constituted by a plurality of electrode pads which are arranged side by side in the direction Y perpendicular to the direction X.

A third terminal portion 11B provided to be electrically connected to the first terminal portion 10B and a fourth terminal portion 11C provided to be electrically connected to the second terminal portion 10C are provided on the front face of the substrate 11 to which the semiconductor substrate 10A is bonded and fixed.

In a plan view seen from the direction perpendicular to the pressure-sensitive face of the semiconductor substrate 10A, the third terminal portion 11B, the first terminal portion 10B, the second terminal portion 10C and the fourth terminal portion 11C are arranged and disposed in the named in the direction X.

Each of the third terminal portion 11B and the fourth terminal portion 11C is constituted by a plurality of electrode pads arranged side by side in the direction Y perpendicular to the direction X. Each of terminals of the third terminal portion 11B corresponds to one of terminals of the first terminal portion 10B. Each of terminals of the fourth terminal portion 11C corresponds to one of terminals of the second terminal portion 10C.

As shown in FIG. 3, each of the terminals of the first terminal portion 10B and a corresponding one of the terminals of the third terminal portion 11B to this terminal are electrically connected to each other through a wire W1 which is a first electrically conductive member. In addition, each of the terminals of the second terminal portion 10C and a corresponding one of the terminals of the fourth terminal portion 11C to this terminal are electrically connected to each other through a wire W2 which is a second electrically conductive member.

Although not shown, a connection terminal connected to each of the terminals of the third terminal portion 11B and a connection terminal connected to each of the terminals of the fourth terminal portion 11C are provided on the substrate 11 to be exposed to the front face of the flexible board 16. These connection terminals are connected to wiring terminals of the flexible board 16.

The wire W1 and the wire W2 are covered with and protected by protective members 13 individually and respectively. For example, an epoxy-based resin, a silicon-based resin, or the like, can be used as each of the protective members 13. A material largely changed in volume due to environmental conditions such as temperature, humidity, etc. is often used as the resin material for protecting each wire.

The pressure-sensitive face of the semiconductor substrate 10A, the protective member 13 for the wire W1 and the protective member 13 for the wire W2 are covered with a front face coating layer 15 for protecting a front face of the pressure pulse wave sensor 1. The front face coating layer 15 is composed, for example, of a silicon-based resin.

The pressure pulse wave sensor 1 configured in the aforementioned manner is put into use so that the pressure-sensitive face of the semiconductor substrate 10A where the pressure-sensitive element array 10D is formed is pressed against a body surface of a living body through the front face coating layer 15 in a state in which the pressure-sensitive element array 10D is positioned right above an artery and the direction X intersects with (preferably intersects perpendicularly to) a traveling direction of the artery. Thus, an electric signal corresponding to a strain applied to the thin portion of the semiconductor substrate 10A, i.e. a signal indicating a pressure fluctuation acting on each pressure-sensitive element S is outputted from the pressure-sensitive element S.

In the blood pressure measurement device 100, the controller 3 determines an optimum pressure-sensitive element and optimum pressing force based on a signal outputted from the pressure pulse wave sensor 1 while using the pressing mechanism 2 to adjust a pressing state of the pressure-sensitive sensor 1 against the body surface. Then, the controller 3 measures a pressure pulse wave based on a signal outputted from the optimum pressure-sensitive element in the optimum pressing force, and calculates biological information such as a blood pressure value, a pulse rate, etc. based on the pressure pulse wave.

As described above, the material largely changed in volume due to a change in temperature or humidity is often used as each of the protective members 13. The pressure pulse wave sensor 1 has the configuration in which the protective members 13 are provided on the opposite end sides of the pressure-sensitive element array 10D in the direction X. For this reason, detection sensitivity of each of the pressure-sensitive elements S of the pressure-sensitive element array 10D is affected by stress caused by the protective members 13 as shown in FIG. 5.

Figure 5:
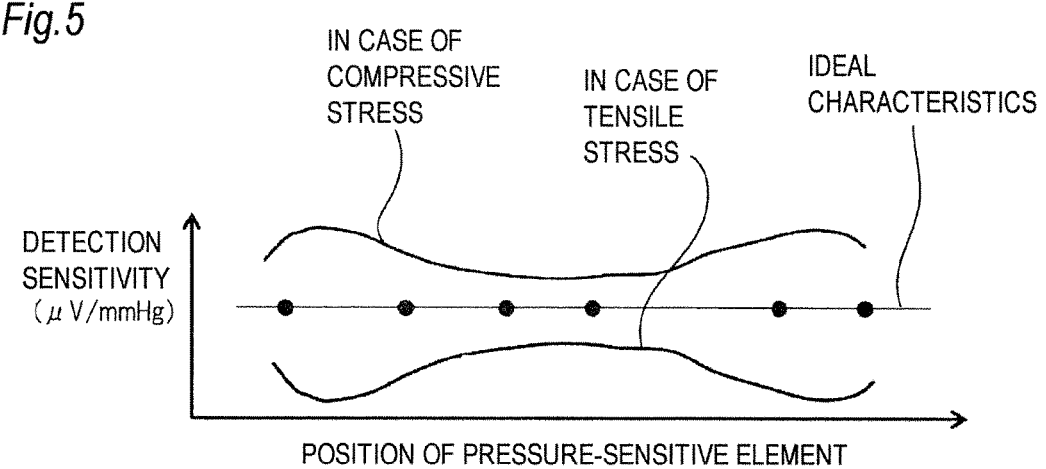
FIG. 5 is a chart for explaining an influence of stress due to each protective member 13.

FIG. 5 shows an ideal sensitivity characteristic in which the detection sensitivity of each of the pressure-sensitive elements S is fixed, a sensitivity characteristic of the pressure-sensitive element array 10D when compressive stress has occurred due to the protective members 13, and a sensitivity characteristic of the pressure-sensitive element array 10D when tensile stress has occurred due to the protective members 13.

In the configuration in which the protective members 13 are provided on the opposite end sides of the pressure-sensitive element array 10D in the direction X as in the pressure-sensitive pulse sensor 1, it is known that a variation in sensitivity is generated between ones of the pressure-sensitive elements S located at positions near to the protective members 13, and ones of the pressure-sensitive elements S located at positions far from the protective members 13 due to stress generated due to deformation of the protective members 13.

Accordingly, it is important to evaluate the sensor chip 10 based on a signal outputted from the pressure-sensitive element array 10D in a state in which the sensor chip 10 is fixed to the substrate 11, the sensor chip 10 and the substrate 11 are electrically connected to each other through the electrically conductive members (wires W1 and W2), and the electrically conductive members are protected by the protective members 13 in the pressure pulse wave sensor 1.

Figure 6A:
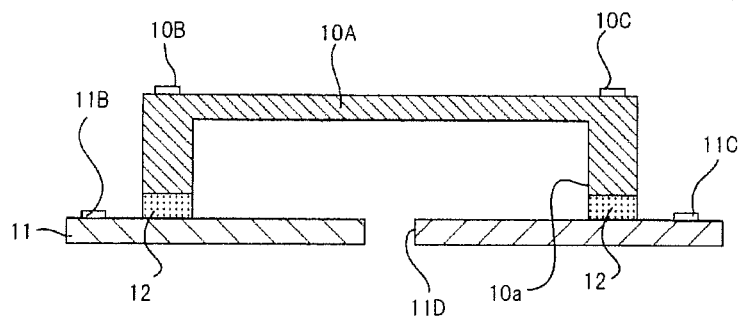
FIGS. 6A, 6B and 6C are views for explaining a method for inspecting the pressure pulse wave sensor 1.
Figure 6B:
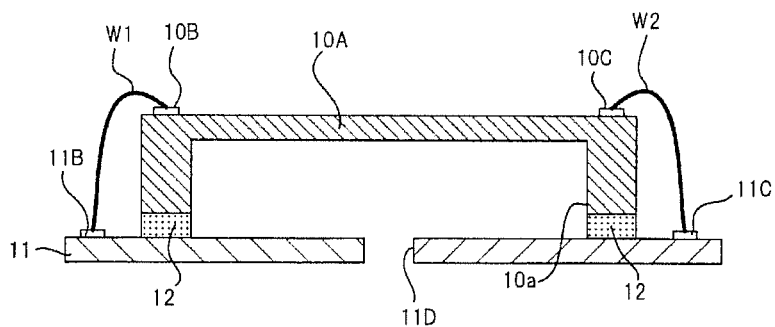
Figure 6C:
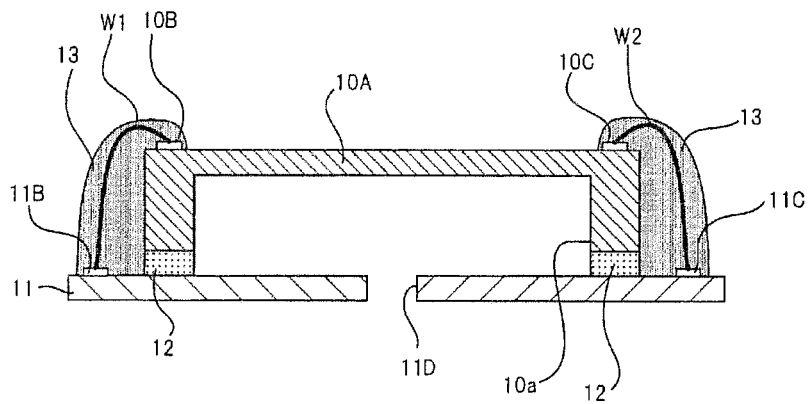
Figure 7:
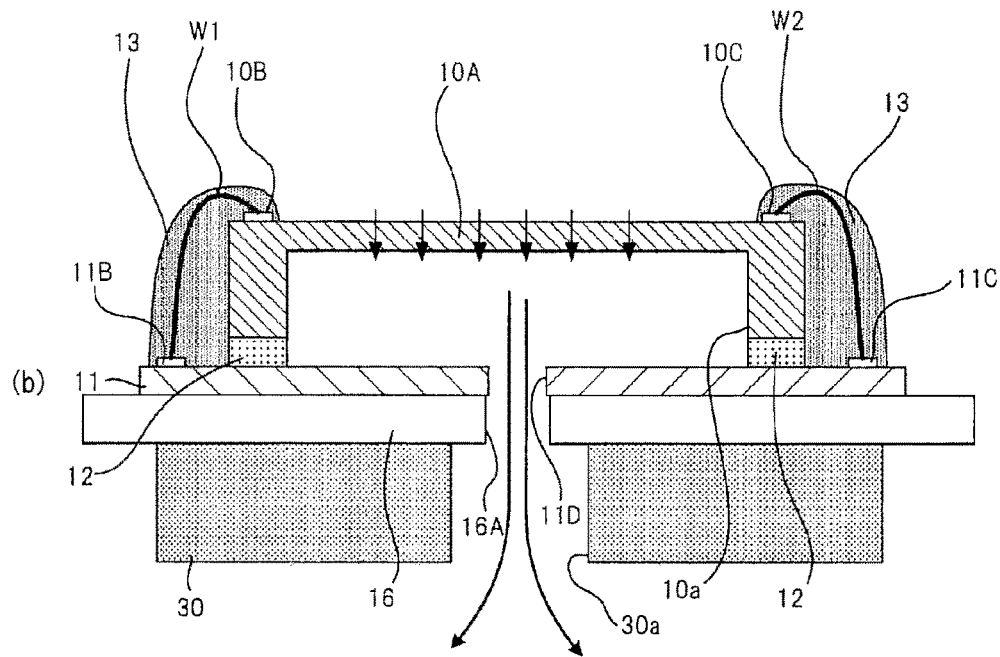
FIG. 7 is a view for explaining the method for inspecting the pressure pulse wave sensor 1.

A method for inspecting the pressure pulse wave sensor 1 will be described below. FIG. 6A to FIG. 7 are views for explaining the method for inspecting the pressure pulse wave sensor 1. FIG. 6A to FIG. 7 correspond to the sectional view of FIG. 3. In FIG. 6A to FIG. 7, constituent elements the same as those in FIG. 3 will be referred to by the same signs correspondingly and respectively.

First, the sensor chip 10 in which the first terminal portion 10B, the second terminal portion 10C and the pressure-sensitive element array 10D are formed on the semiconductor substrate 10A, and the substrate 11 on which the third terminal portion 11B and the fourth terminal portion 11C are formed are prepared. As shown in FIG. 6A, the sensor chip 10 is fixed to the front face of the substrate 11 by the adhesive material 12 in a state in which the recess 10a is overlapped with a region of the substrate 11 including the through hole 11D.

Next, a wire bonding step is performed. As shown in FIG. 6B, each of the terminals of the first terminal portion 10B and a corresponding one of the terminals of the third terminal portion 11B to this terminal are connected to each other by the wire W1. In addition, each of the terminals of the second terminal portion 10C and a corresponding one of the terminals of the fourth terminal portion 11C to this terminal are connected to each other by the wire W2.

Next, a wire protection step is performed. As shown in FIG. 6C, the wire W1 and the wire W2 are covered with and protected by the protective members 13 respectively.

Next, in a state in which the through hole 11D of the sensor chip which is being built as shown in FIG. 6C, and the through hole 16A of the flexible board 16 are overlapped with each other, the sensor chip is mounted on the flexible board 16. Thus, the connector 16C of the flexible board 16 and the pressure-sensitive element array 10D are electrically connected to each other.

In this state, an inspection device which performs processing to acquire an output signal from each of the pressure-sensitive elements S of the pressure-sensitive element array 10D and perform characteristic evaluation on the sensor chip 10 based on the acquired output signal is connected to the connector 16C.

Further, as shown in FIG. 7, the flexible board 16 is set on a suction device 30 having a suction hole 30a for sucking air so that the suction hole 30a of the suction device 30 and the through hole 16A overlap each other. When the suction device 30 sucks air through the suction hole 30a, pressure of the space partitioned by the semiconductor substrate 10A, the adhesive material 12 and the substrate 11 is reduced. As a result, negative pressure is applied to the thin portion of the semiconductor substrate 10A where the pressure-sensitive element array 10D is formed.

In the state in which the negative pressure is applied, the aforementioned inspection device acquires an output signal from each of the pressure-sensitive elements S and performs characteristic evaluation on the sensor chip 10 in accordance with a predetermined evaluation algorithm. The characteristic evaluation is performed while temperature and humidity of an environment in which the pressure-pulse wave sensor 1 which is being built is placed are changed.

For example, a variation in detection sensitivity among the respective pressure-sensitive elements S of the pressure-sensitive element array 10D is obtained in various environments. Thus, any sensor chip in which the variation falls into a permissible range is determined as accepted.

The sensor chip which is being built and has been determined as accepted is moved to a front face coating step. In the front face coating step, a protective material made of the silicon-based resin or the like covers the protective members 13 at the two places and the exposed face of the sensor chip 10 to thereby form the front face coating layer 15. The front face coating layer 15 covers and protects the sensor chip 10 and the protective members 13 to thereby constitute a protective layer. By the front face coating step, the pressure pulse wave sensor 1 is completed.

According to the aforementioned inspection method, the characteristic evaluation is performed on the sensor chip 10 in the state in which the protective members 13 which are likely to affect the characteristic of the pressure-sensitive element array 10D have been formed. Thus, an influence of a change in usage environment on detection accuracy of a pressure pulse wave can be known, and the pressure pulse wave sensor having higher detection accuracy of the pressure pulse wave can be manufactured.

In addition, according to the aforementioned inspection method, the characteristic evaluation can be performed on the sensor chip 10 without touching the semiconductor substrate 10A. For this reason, the characteristic evaluation can be performed before the front face coating layer 15 is formed. Since the front face coating layer 15 is not formed on any rejected sensor chip, production efficiency can be improved.

In the aforementioned description, the characteristic evaluation is performed on the sensor chip 10 after the protective members 13 have been formed. As a modification of the example, the characteristic evaluation may be performed on the sensor chip 10 in a state in which the substrate 11 in the state of FIG. 6B has been mounted onto the flexible board 16 and air has been sucked through the through hole 11D and the through hole 16A.

There is a possibility that the characteristic of the sensor chip 10 may change due to a variation in coating amount of the adhesive material 12 in the state in which the sensor chip 10 is fixed to the substrate 11. In addition, when the material changed in volume due to the temperature and the humidity is used as the adhesive material 12, it is conceived that the characteristic of the sensor chip 10 may change due to the usage environment.

Therefore, also when the characteristic evaluation is performed on the sensor chip 10 by the inspection device in a state in which negative pressure is applied to the pressure-sensitive face by the suction device 30 in a stage where the protective members 13 have not been formed, an influence of a change in usage environment on detection accuracy of a pressure pulse wave can be known, and the pressure pulse wave sensor having higher detection accuracy of the pressure pulse wave can be manufactured.

In addition, according to the modification, the characteristic evaluation is performed in the stage where the protective members 13 have not been formed. Accordingly, any rejected sensor chip can be specified in an early stage, so that production efficiency can be improved.

Incidentally, in the modification, the protective members 13 are formed after the characteristic evaluation is performed on the sensor chip 10. However, when, for example, a material little changed in volume due to the temperature and the humidity is used as each of the protective members 13, the characteristic of the sensor chip 10 can be prevented from being changed largely after the characteristic evaluation. Consequently, performance can be secured. In addition, in the modification, after the protective members 13 are formed, the protective material made of the resin etc. covers the exposed face of the sensor chip 10 and the protective members 13 to thereby form the front face coating layer 15. As a result, the pressure pulse wave sensor is completed.

In the inspection method shown in FIGS. 6A to 6C, the degree of freedom for selecting the material of the protective members 13 is increased, and inspection can be performed in consideration of the influence of both the adhesive material 12 and the protective members 13 on the characteristic of the pressure-sensitive element array 10D. Accordingly, the inspection method shown in FIGS. 6A to 6C can be carried out particularly preferably.

The pressure pulse wave sensor 1 is configured to be provided with chip-side terminal portions and substrate-side terminal portions. The chip-side terminal portions constituted by the first terminal portion 10B and the second terminal portion 10C are provided on the opposite end portions of the pressure-sensitive face of the semiconductor substrate 10A in the direction X. The substrate-side terminal portions are constituted by the third terminal portion 11B and the fourth terminal portion 11C corresponding to the first terminal portion 10B and the second terminal portion 10C respectively.

Figure 8:
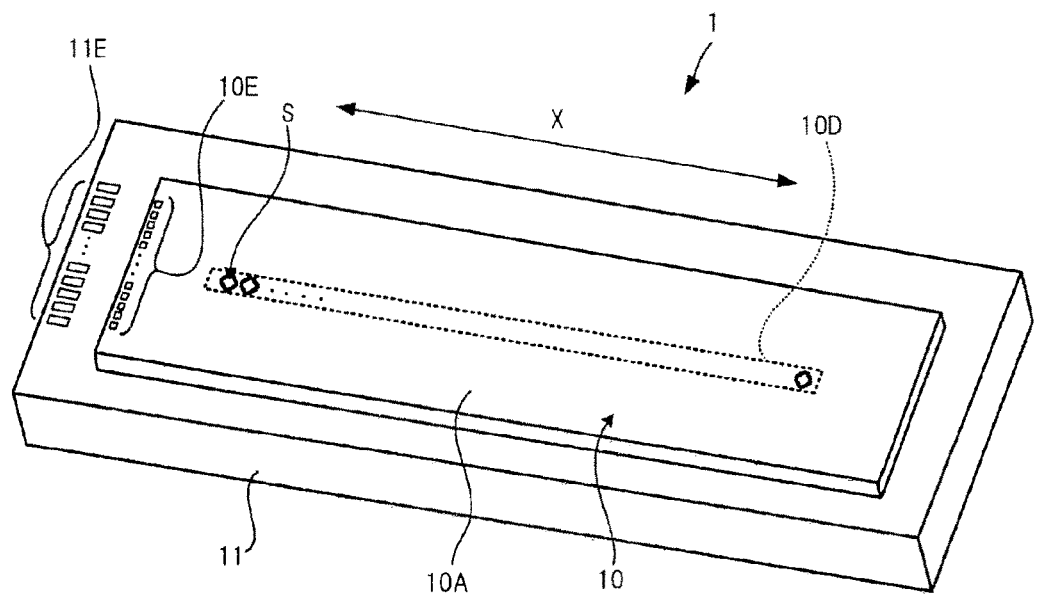
FIG. 8 is a view showing a modification of the perspective view of the pressure pulse wave sensor 1 shown in FIG. 4.

As a modification of the example, configuration may be made so that a chip-side terminal portion 10E including terminals electrically connected to the pressure-sensitive elements S respectively is provided only on one of the opposite end portions of the pressure-sensitive face of the semiconductor substrate 10A in the direction X, as shown in FIG. 8.

In this case, a substrate-side terminal portion 11E including terminals provided to be electrically connected to the terminals of the chip-side terminal portion 10E respectively may be formed on the front face of the substrate 11 which is opposed to the pressure-sensitive element array 10D in the direction X with the chip-side terminal portion 10E as a border.

Also in the case of the configuration shown in FIG. 8, due to stress generated due to deformation of a protective member covering an electrically conductive member connecting the chip-side terminal portion 10E and the substrate-side terminal portion 11E to each other, there is a possibility that a variation in sensitivity is generated between any of the pressure-sensitive elements S located at a position near to the protective member and any of the pressure-sensitive elements S located at a position far from the protective member. Therefore, the inspection method according to the embodiment which can inspect the influence of the protective member on the sensor chip 10 is effective.

Incidentally, in the configuration in which the chip-side terminal portions constituted by the first terminal portion 10B and the second terminal portion 10C are provided on the opposite end portions of the pressure-sensitive face of the semiconductor substrate 10A in the direction X, as shown in FIG. 4, the width of the sensor chip 10 in the direction Y does not have to be increased. Accordingly, the configuration is favorable for reduction of the size of the pressure pulse wave sensor 1.

It should be conceived that all the points in the embodiment disclosed this time are not limited but merely exemplified. The scope of the invention is defined not by the aforementioned description but by the scope of Claims. All changes having equivalent meaning to the scope of Claims and within the scope of Claims are intended to be included in the scope of the invention.

For example, the wrist-worn type blood pressure measurement device for detecting a pressure pulse wave of a radial artery of a wrist has been described so far. However, any other blood pressure measurement device applied to a carotid artery or a dorsalis pedis artery may be used alternatively.

In addition, each of the pressure-sensitive elements S for detecting contact pressure is not limited to an element using a bridge circuit and a diaphragm. However, any other element having a well-known configuration may be used as the pressure-sensitive element S. In addition, the blood pressure measurement device 100 is designed to have two pressure pulse wave sensors 1. However, as long as at least one pressure pulse wave sensor 1 is provided, the pressure pulse wave can be detected and the biological information can be measured.

In addition, connection between each of the terminals of the first terminal portion 10B and a corresponding one of the terminals of the third terminal portion 11B to this terminal is not necessarily performed by a wire but may be performed by an electrically conductive member such as an electrically conductive paste. Similarly, connection between each of the terminals of the second terminal portion 10C and a corresponding of the terminals of the fourth terminal portion 11C to this terminal is not necessarily performed by a wire but may be performed by an electrically conductive member such as an electrically conductive paste.

Even when the connection is performed by any electrically conductive member, a protective member 13 for protecting the wire formed of the electrically conductive member is required. Therefore, the invention is effective.

In addition, the characteristic evaluation is performed on the sensor chip 10 in the state where the connector 16C of the flexible board 16 and the inspection device are connected to each other. However, the flexible board 16 may be replaced by an inspection probe which is brought into contact with the connection terminals exposed in a back face of the substrate 11 in the state of FIG. 6C, so as to extract a signal from the sensor chip 10. In this case, the flexible board does not have to be used wastefully in any rejected chip sensor.

As described above, the following matters are disclosed in the description of the present invention.

The disclosed method for inspecting a pressure pulse wave sensor is a method for inspecting a pressure pulse wave sensor which includes a sensor chip and a substrate, the sensor chip including a pressure-sensitive element array constituted by a plurality of pressure-sensitive elements arranged in one direction, and a chip-side terminal portion electrically connected to the pressure-sensitive element array, the sensor chip put into use so that a pressure-sensitive face of the sensor chip where the pressure-sensitive element array is formed is pressed against a body surface of a living body in a state in which the one direction intersects with a traveling direction of an artery of the living body, the sensor chip fixed to the substrate, the substrate including a through hole, wherein the sensor chip includes a recess which is recessed in a direction perpendicular to the pressure-sensitive face, and the pressure-sensitive element array is formed in a portion of the sensor chip whose thickness is reduced in the direction due to the recess, the method including: a first step of bonding and fixing the sensor chip onto the substrate so that the recess communicates with atmospheric air through only the through hole of the substrate; a second step of connecting a substrate-side terminal portion of the substrate to which the sensor chip is bonded and fixed, and the chip-side terminal portion through an electrically conductive member; and a third step of performing characteristic evaluation on the sensor chip, after the second step, based on a signal outputted from the substrate-side terminal portion in a state in which air is sucked through the through hole of the substrate to thereby apply negative pressure to the pressure-sensitive face.

In the disclosed method for inspecting the pressure pulse wave sensor, the chip-side terminal portion may include a first terminal portion and a second terminal portion which are disposed respectively on opposite end portions of the pressure-sensitive face in the one direction, the substrate-side terminal portion may include a third terminal portion and a fourth terminal portion which are formed on a face of the substrate to which the sensor chip is bonded and fixed, the third terminal portion, the first terminal portion, the second terminal portion and the fourth terminal portion may be arranged in this order in the one direction in a plan view which is seen from the direction perpendicular to the pressure-sensitive face, the first terminal portion and the third terminal portion may be connected through a first electrically conductive member and the second terminal portion and the fourth terminal portion may be connected through a second electrically conductive member in the second step, and the method may further include a fourth step of covering the first electrically conductive member and the second electrically conductive member which are formed in the second step, with protective members respectively prior to the third step.

The disclosed method for manufacturing a pressure pulse wave sensor is a method for manufacturing a pressure pulse wave sensor which includes a sensor chip and a substrate, the sensor chip including a pressure-sensitive element array constituted by a plurality of pressure-sensitive elements arranged in one direction, and a chip-side terminal portion electrically connected to the pressure-sensitive element array, the sensor chip put into use so that a pressure-sensitive face of the sensor chip where the pressure-sensitive element array is formed is pressed against a body surface of a living body in a state in which the one direction intersects with a traveling direction of an artery of the living body, the sensor chip fixed to the substrate, the substrate having a through hole, wherein: the sensor chip includes a recess which is recessed in a direction perpendicular to the pressure-sensitive face, and the pressure-sensitive element array is formed in a portion of the sensor chip whose thickness is reduced in the direction due to the recess, the method including: a first step of bonding and fixing the sensor chip onto the substrate so that the recess communicates with atmospheric air through only the through hole of the substrate; a second step of connecting a substrate-side terminal portion of the substrate to which the sensor chip is bonded and fixed, and the chip-side terminal portion through an electrically conductive member; a third step of performing characteristic evaluation on the sensor chip after the second step based on a signal outputted from the substrate-side terminal portion in a state in which air is sucked through the through hole of the substrate to thereby apply negative pressure to the pressure-sensitive face; and a fifth step of forming a protective layer protecting both the sensor chip which is determined as accepted based on a result of the characteristic evaluation of the third step, and the electrically conductive member which connects the chip-side terminal portion of the sensor chip and the substrate-side terminal portion.

In the disclosed method for manufacturing the pressure pulse wave sensor, the chip-side terminal portion may include a first terminal portion and a second terminal portion which are disposed respectively on opposite end portions of the pressure-sensitive face in the one direction, the substrate-side terminal portion may include a third terminal portion and a fourth terminal portion which are formed on a face of the substrate to which the sensor chip is bonded and fixed, the third terminal portion, the first terminal portion, the second terminal portion and the fourth terminal portion may be arranged in this order in the one direction in a plan view which is seen from the direction perpendicular to the pressure-sensitive face, the first terminal portion and the third terminal portion may be connected through a first electrically conductive member and the second terminal portion and the fourth terminal portion may be connected through a second electrically conductive member in the second step, the method may further include a fourth step of covering the first electrically conductive member and the second electrically conductive member which are formed in the second step, with protective members respectively prior to the third step, and in the fifth step, a protective material may cover an exposed face of the sensor chip and the protective members to form the protective layer.

According to the invention, it is possible to provide an inspection method and a manufacturing method of a pressure pulse wave sensor, in which it is possible to know an influence of a change in usage environment on detection accuracy of a pressure pulse wave.

Although the invention has been described above based on a specific embodiment, the invention is not limited to the embodiment. Various changes may be however made on the invention without departing from the technical concept of the disclosed invention.

What is claimed is:

1. A method for inspecting a pressure pulse wave sensor which includes a sensor chip and a substrate, the sensor chip including a pressure-sensitive element array constituted by a plurality of pressure-sensitive elements arranged in one direction, the sensor chip put into use so that a pressure-sensitive face of the sensor chip where the pressure-sensitive element array is formed is pressed against a body surface of a living body in a state in which the one direction intersects with a traveling direction of an artery of the living body, the sensor chip fixed to the substrate, wherein
the substrate includes a through hole and a substrate-side terminal portion,
the sensor chip includes a recess which is recessed in a direction perpendicular to the pressure-sensitive face and on an opposite side to the pressure-sensitive face, and the pressure-sensitive element array is formed on the pressure-sensitive face in a portion of the sensor chip whose thickness is reduced in the perpendicular direction due to the recess, and
the sensor chip further includes a chip-side terminal portion which is electrically connected to the pressure-sensitive element array and which is provided at one or each of opposite ends of the pressure-sensitive element array extending in the one direction,
the method comprising:
bonding and fixing the sensor chip onto the substrate so that the recess communicates with atmospheric air through only the through hole of the substrate;
connecting the substrate-side terminal portion of the substrate to which the sensor chip is bonded and fixed, and the chip-side terminal portion through an electrically conductive member;
covering the electrically conductive member with a protective member; and
performing characteristic evaluation about a variation among the plurality of pressure-sensitive elements of the sensor chip, after covering the electrically conductive member with the protective member, based on a signal outputted from the substrate-side terminal portion in a state in which air is sucked through the through hole of the substrate to thereby apply negative pressure to the pressure-sensitive face.

2. The method for inspecting the pressure pulse wave sensor according to claim 1, wherein
the chip-side terminal portion includes a first terminal portion and a second terminal portion which are disposed respectively on opposite end portions of the pressure-sensitive face in the one direction,
the substrate-side terminal portion includes a third terminal portion and a fourth terminal portion which are formed on a face of the substrate to which the sensor chip is bonded and fixed,
the third terminal portion, the first terminal portion, the second terminal portion and the fourth terminal portion are arranged in this order in the one direction in a plan view which is seen from the direction perpendicular to the pressure-sensitive face,
the first terminal portion and the third terminal portion are connected through a first electrically conductive member and the second terminal portion and the fourth terminal portion are connected through a second electrically conductive member, and
the first electrically conductive member and the second electrically conductive member are covered with protective members respectively.

3. A method for manufacturing a pressure pulse wave sensor which includes a sensor chip and a substrate, the sensor chip including a pressure-sensitive element array constituted by a plurality of pressure-sensitive elements arranged in one direction, the sensor chip put into use so that a pressure-sensitive face of the sensor chip where the pressure-sensitive element array is formed is pressed against a body surface of a living body in a state in which the one direction intersects with a traveling direction of an artery of the living body, the sensor chip fixed to the substrate, wherein
a through hole and a substrate-side terminal portion are formed in the substrate,
a recess which is recessed in a direction perpendicular to the pressure-sensitive face and on an opposite side to the pressure-sensitive face is formed in the sensor chip, and the pressure-sensitive element array is formed on the pressure-sensitive face in a portion of the sensor chip whose thickness is reduced in the perpendicular direction due to the recess, and
a chip-side terminal portion which is electrically connected to the pressure-sensitive element array is further formed at one or each of opposite ends of the pressure-sensitive element array extending in the one direction in the sensor chip,
the method comprising:
bonding and fixing the sensor chip onto the substrate so that the recess communicates with atmospheric air through only the through hole of the substrate;
connecting the substrate-side terminal portion of the substrate to which the sensor chip is bonded and fixed, and the chip-side terminal portion through an electrically conductive member;
covering the electrically conductive member with a protective member;
performing characteristic evaluation about a variation among the plurality of pressure-sensitive elements of the sensor chip, after covering the electrically conductive member with the protective member, based on a signal outputted from the substrate-side terminal portion in a state in which air is sucked through the through hole of the substrate to thereby apply negative pressure to the pressure-sensitive face; and
forming a protective layer protecting both the sensor chip which is determined as accepted based on a result of the characteristic evaluation, and the protective member which covers the electrically conductive member which connects the chip-side terminal portion of the sensor chip and the substrate-side terminal portion.

4. The method for manufacturing the pressure pulse wave sensor according to claim 3, wherein
the chip-side terminal portion includes a first terminal portion and a second terminal portion which are disposed respectively on opposite end portions of the pressure-sensitive face in the one direction, the substrate-side terminal portion includes a third terminal portion and a fourth terminal portion which are formed on a face of the substrate to which the sensor chip is bonded and fixed, the third terminal portion, the first terminal portion, the second terminal portion and the fourth terminal portion are arranged in this order in the one direction in a plan view which is seen from the direction perpendicular to the pressure-sensitive face, the first terminal portion and the third terminal portion are connected through a first electrically conductive member and the second terminal portion and the fourth terminal portion are connected through a second electrically conductive member, the first electrically conductive member and the second electrically conductive member are covered with protective members respectively, and a protective material covers an exposed face of the sensor chip and the protective members to form the protective layer.

* * * * *